United States Patent [19]

Yamada

[11] Patent Number: 4,753,203
[45] Date of Patent: Jun. 28, 1988

[54] AIR/FUEL RATIO SENSOR APPARATUS FOR USE WITH INTERNAL COMBUSTION ENGINE

[75] Inventor: Tetsusyo Yamada, Aichi, Japan

[73] Assignee: NGK Spark Plug Co., Ltd., Nagoya, Japan

[21] Appl. No.: 831,734

[22] Filed: Feb. 21, 1986

[30] Foreign Application Priority Data

Feb. 25, 1985 [JP] Japan ................................ 60-36031

[51] Int. Cl.⁴ ............................................. F02B 3/00
[52] U.S. Cl. ..................................... 123/440; 123/479
[58] Field of Search ................ 123/493, 489, 440, 479

[56] References Cited

U.S. PATENT DOCUMENTS 4,363,306 12/1982 Sone ..................................... 123/440
4,601,809 7/1986 Kitahara ............................... 123/489

Primary Examiner—Ronald B. Cox
Attorney, Agent, or Firm—Sughrue, Mion, Zinn, Macpeak, and Seas

[57] ABSTRACT

An air/fuel ratio sensor apparatus which is capable of detecting deterioration of the sensing elements and correcting the output of the apparatus accordingly. The apparatus includes two sensing elements and a closed compartment of which the two sensing elements define at least portions. One of the sensing elements is used as an oxygen concentration measuring cell, and the other as an oxygen pump cell. When the internal combustion engine with which the sensor is associated is running without fuel supply, a reference voltage used for controlling the oxygen pumping current is set to a smaller value than that employed when the engine is running with a fuel supply. Deterioration of the sensing elements is then detected by comparing the output air/fuel ratio signal produced at that time with a preset fixed value.

1 Claim, 6 Drawing Sheets

AIR/FUEL RATIO SENSOR APPARATUS FOR USE WITH INTERNAL COMBUSTION ENGINE

BACKGROUND OF THE INVENTION

The present invention relates to an air/fuel ratio sensor for use with an internal combustion engine and, more particularly, to an air/fuel ratio sensor capable of detecting deterioration of the sensing elements that may occur when the engine is operated without a fuel supply.

A conventional air/fuel (A/F) ratio sensor for use with an internal combustion engine employs two sensing elements each consisting of an oxygen-ion-conductive solid electrolyte having a porous electrode formed on both sides. This sensor has the ability to detect the concentration of oxygen in the exhaust gas from the internal combustion engine and produce an A/F signal.

In a typical sensor of this type, the two sensing elements are disposed in a face-to-face relationship with a small gap therebetween so as to provide a closed compartment that accepts a limited inflow of the exhaust gas. One of the two sensing elements is used as an oxygen concentration electrochemical cell while the other unit works as an oxygen pump. The pump current flowing through the oxygen pump is controlled such that the electromotive force generated by the electrochemical cell is maintained at a predetermined level and the resultant pump current is detected as an A/F ratio signal.

Air/fuel sensors may also be used with modern internal combustion engines to perform electronic feedback control over the fuel injection (A/F ratio). One type of electronic control performed on these engines is fuel cutting control in which the fuel supply to the engine is stopped when the vehicle is slowing down or running under low-load conditions.

The above-described conventional A/F ratio sensor designed to control the pump current and produce an associated A/F ratio signal may be employed to perform A/F ratio control on an internal combustion engine adapted for fuel cutting control. When a vehicle having such an engine and running at full throttle slows down, fuel cutting control is started to stop fuel injection. Since no fuel is injected into the engine, there is no need to perform control of the A/F ratio. But, in fact, the A/F ratio sensor will continue to perform control of the pump current, and hence the concentration of atmospheric air is detected as an associated A/F ratio signal.

The conventional A/F ratio sensor which will control the pump current and produce an associated A/F ratio signal is required to have a sufficiently accurate response that it is capable of precise A/F ratio detection in the vicinity of the stoichiometric A/F ratio where the exhaust gas has a comparatively low oxygen level. To this end, the A/F ratio sensor is provided with the capability of controlling the pump current flowing through the oxygen pump so as to produce a great difference between the oxygen partial pressure in the exhaust and that in the closed compartment in order to ensure that the oxygen concentration electrochemical cell will produce a predetermined high output voltage. Because of this design, if atmospheric air flows into the exhaust pipe when the car is running with no fuel supply, a large current will flow into the oxygen pump so that a large volume of oxygen is pumped out of the closed compartment. This, however, accelerates the deterioration of the oxygen pump and increases the change of failure in providing accurate A/F ratio detection.

In order to avoid this problem, a control circuit may be configured such that the maximum pump current flowing when the car is operating without fuel supply is within allowable limits. In this case, however, the sensitivity or response of the sensor will decrease with the decreasing concentration of oxygen in the exhaust, thereby making it difficult to accomplish accurate A/F ratio detection in the vicinity of the stoichiometric value.

In an A/F ratio detector, the sensing elements deteriorate as a result of prolonged exposure to the hot exhaust gas. In addition, dust particles may be deposited on the sensing elements for some reason. In either case, the affected sensing elements will produce an incorrect A/F ratio signal that cannot be utilized for the purpose of accurately controlling the A/F ratio of the exhaust from the internal combustion engine.

SUMMARY OF THE INVENTION

The present invention has been accomplished on the basis of the fact that when the vehicle is running without fuel supply, there is no need to detect the A/F ratio signal and that atmospheric air will flow into the exhaust pipe.

The principal purpose, therefore, of the present invention is to provide an A/F ratio detector for use with an internal combustion engine that is designed to detect deterioration of the sensing elements on the basis of the A/F ratio signal being produced when the car is running without fuel supply, which detector is protected against deterioration of the oxygen pump that may result from the passage of a large pump current when such detection is performed. The A/F ratio of the present invention enables precise and correct control of the A/F ratio of the exhaust from the internal combustion engine.

The above-stated object of the present invention is attained in accordance with the invention by two embodiments. The sensor of the first embodiment, being shown in FIG. 1, is an A/F ratio sensor for use with an internal combustion engine, and it comprises:

two sensing elements, M1 and M2, each consisting of an oxygen ion-conductive solid electrolyte having a porous electrode formed on both sides;

a closed compartment M3 that limits the inflow of the exhaust by utilizing at least said two sensing elements M1 and M2;

pump current control circuit means M4 which, by using M1 as an oxygen concentration electrochemical cell and M2 as an oxygen pump, controls the pump current flowing through said oxygen pump M2 such that the electromotive force generated by said oxygen concentration electrochemical cell M1 will be maintained at a present reference voltage; and A/F ratio signal detecting circuit means M5 that detects the controlled pump current and produces an associated A/F ratio signal, said sensor further including:

reference voltage changing circuit means M6 which, when the internal combustion engine is running without fuel supply, will change the reference voltage for said pump current control means M4 to a value smaller than what is used when the engine is running with fuel supply; and deterioration detecting circuit means M7 which, when the engine is running without fuel supply, will detect any deterioration of said two sensing elements M1 and M2 by comparing the A/F ratio signal produced from said A/F ratio signal detecting means M5 with a present reference value.

The sensor of the second embodiment, being shown in FIG. 2, adds to the first embodiment correction coefficient setting means M8 which, when deterioration of the sensing elements M1 and M2 is detected by the means M7, will set a coefficient for correcting the A/F ratio signal that is to be detected while the engine is running with fuel supply on the basis of both the A/F ratio signal detected while the engine is running without fuel supply and the reference value.

Typical examples of the oxygen-ion-conductive solid electrolyte which forms the principal component of the two sensing elements M1 and M2 are a solid solution of zirconia and yttria, and a solid solution of zirconia and calcia. Other usable materials include solid solutions of cerium dioxide, thorium dioxide and hafnium dioxide, a solid solution of the perovskite-type oxide, and a solid solution of a trivalent metal oxide. The porous electrode formed on each side of the solid electrolyte may be made of platinum, rhodium, and other oxidation catalyzing metals.

The porous electrode may be formed by various methods. In one method, a powder of a suitable oxidation catalyzing metal that is used as the principal component is worked into paste by mixing with a powder of the ceramic material of which the solid electrolyte is made, and the paste is printed in a predetermined pattern on the solid electrolyte by a thick-film deposition technique, followed by the sintering of the printed coat. In another method, the powder mixture is applied onto the solid electrolyte by a suitable thin-film depositing technique such as flame spraying, chemical plating or evaporation, and the resulting electrode layer is preferably coated with a porous protective layer (e.g. alumina, spinnel, zirconia or mullite) by the thick-film process. It is also preferable that the porous layer on the electrode facing the diffusion compartment be provided with the oxidation catalyzing action by dispersing platinum, rhodium or other catalyst metals within said porous layer.

Of the two sensing elements M1 and M2 fabricated by the procedures described above, M1 is employed as an oxygen concentration electrochemical cell. The operating mechanism of the cell is as follows: when an oxygen-ion-conductive solid electrolyte is placed under the appropriate temperature conditions (e.g., 400° C. if the solid electrolyte is zirconia), oxygen ions will be transferred through the solid electrolyte from its surface where the oxygen partial pressure is high to the area where the oxygen partial pressure is low, and the differential oxygen partial pressure existing between oxygen gas-permeable electrodes attached to the solid electrolyte can be detected as a voltage (electromotive force). In the apparatus of the present invention, a voltage is established in accordance with the difference between the concentration of oxygen in the closed compartment that accepts a limited inflow of the exhaust and the oxygen partial pressure of the ambient atmosphere (either the exhaust or the atmospheric air).

The other sensing element M2 is employed as an oxygen pump and operates utilizing the transfer of oxygen ions through an oxygen-ion-conductive solid electrolyte upon voltage application. When a voltage is applied between two electrodes on the solid electrolyte, oxygen is pumped out of the closed compartment.

If the oxygen in the closed compartment is pumped out with the oxygen pump and if the current flowing through the pump (pumping current) is controlled by the pump current control means M4 so that the voltage generated by the oxygen concentration electrochemical cell is maintained at a predetermined value, the resulting pumping current may be detected by the A/F ratio signal detection means M5 to thus obtain an A/F ratio signal in accordance with the concentration of oxygen in the exhaust gas.

The reference voltage changing means M6 functions to reduce the reference voltage for the pump current control means M4 when the engine is running without fuel supply. If an A/F ratio signal continues to be detected using the high normal reference voltage for pump current control, even if the atmospheric air is introduced through the exhaust pipe when the engine is running without fuel supply, an excessively large pumping current will flow to degrade the performance of the oxygen pump. In order to minimize the increase in pumping current, the means M6 reduces the reference voltage for the pump current control means when the engine is running without fuel supply.

The deterioration detecting means M7 functions to detect any deterioration of sensing element M1 or M2 on the basis of the A/F ratio signal that is obtained at the A/F ratio detection means M5 when the engine is operating without fuel supply, or the A/F ratio signal associated with the pumping current that is controlled by the means M4 with reference to the voltage set as a result of alteration by the reference voltage changing means M6.

The mechanism behind the detecting operation of means M7 is as follows: When the engine is running without fuel supply, atmospheric air is introduced into the exhaust pipe. If both sensing elements M1 and M2 are normal, the A/F ratio signal obtained will maintain a constant value (reference level). On the other hand, if the obtained A/F ratio signal does not coincide with the reference level or is not within allowable limits of the reference level, either M1 or M2 is regarded as having deteriorated.

The sensor apparatus in accordance with the second embodiment of the present invention is characterized by incorporating the correction coefficient setting the means M8 which, when the means M7 has detected deterioration of M1 or M2, sets the coefficient for correcting the A/F ratio signal that is to be delivered from the detection means M5 when the engine is running with fuel supply (i.e., during execution of A/F ratio control mode), and the setting of this coefficient is dependent on the degree of deterioration of M1 or M2. For the purposes of the present invention, the coefficient of correction is determined on the basis of both the A/F ratio signal obtained when the engine is running without fuel supply and the reference value for that signal. The reasons for this are as follows: the molecules of oxygen in the closed compartment M3 are assumed to have a diffusion coefficient $\sigma$, which is represented by:

$$\sigma = \frac{Ip}{4e(P_{o,exh} - P_{o,v})}$$

$$\sigma = \frac{Ip}{4eP_{o,exh}\{1 - (P_{o,v}/P_{o,exh})\}}$$

where $P_{o,exh}$: oxygen partial pressure in the exhaust,
$P_{o,v}$: oxygen partial pressure in the closed compartment,
Ip: pumping current, and
e: electron charge.

This equation shows that is proportional to Ip if $P_{o,exh}$ is constant and if a constant output voltage is produced from M1, providing a constant value of $P_{o,v}/P_{o,exh}$ when the engine is running without fuel supply. Therefore, if is changed as a result of, for example, deposition of dust particles at the exhaust flow limiting opening in the closed compartment M3, the amount of its change can be determined in terms of the change in the pumping current Ip.

In the A/F ratio sensor for use with an internal combustion engine in accordance with the first embodiment of the present invention, the reference voltage for the pump current control means M4 that is used when the engine is running without fuel supply is adjusted by the reference voltage changing means M6 to a value smaller than the level used in the case where the engine is running with fuel supply. This prevents the passage through M2 of a pumping current that is large enough to cause deterioration of that oxygen pump. When the engine is running without fuel supply, the detection means M7 detects deterioration of M1 or M2 on the basis of the A/F ratio signal detected by the A/F ratio detection means M5. Therefore, there is no possibility that the detected signal will be employed as a basis for performing control of the A/F ratio of the exhaust from the engine running with no fuel supply.

The A/F ratio sensor for use with an internal combustion engine in accordance with the second embodiment is the same as the design of the first embodiment except that it incorporates the correction coefficient setting means M8. When any deterioration of sensing element M1 or M2 is detected by the means M7, the coefficient for correcting the A/F ratio signal is recomputed so that the deterioration of M1 or M2 is compensated for to provide a A/F ratio signal that gives a correct indication of the concentration of oxygen in the exhaust. Therefore, the A/F ratio of the exhaust from the internal combustion engine can be precisely controlled despite deterioration of the sensing element M1 or M2.

BRIEF DESCRIPTION OF THE DRAWINGS

FIGS. 3 to 8 show an embodiment of an A/F ratio detector incorporating the concepts of the present invention in accordance with both its first and second embodiments, wherein FIG. 3 is a schematic diagram depicting the engine on which the sensor is installed, FIG. 4 is a cross section showing the basic construction of the oxygen sensor 4 as attached to the exhaust manifold, FIG. 5 is a perspective view of the oxygen concentration electrochemical cell, FIG. 6 is an electric circuit diagram of the A/F ratio detector circuit, FIG. 7 is a flow chart showing the sequence of detecting deterioration of the oxygen sensor, and FIG. 8 is a graph showing various settings of the reference voltage $V_s$.

DESCRIPTION OF THE PREFERRED EMBODIMENTS

The preferred embodiments of the present invention are hereunder more specifically described with reference to the accompanying drawings.

Figure 1:
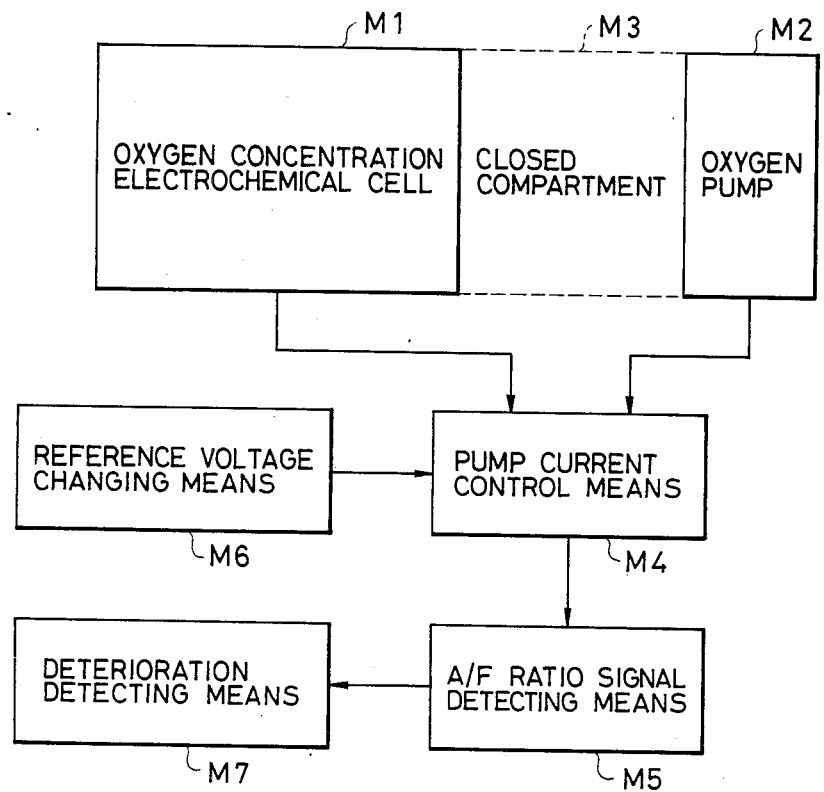
FIG. 1 is a block diagram of an A/F ratio sensor in accordance with a first embodiment of the present invention.
Figure 2:
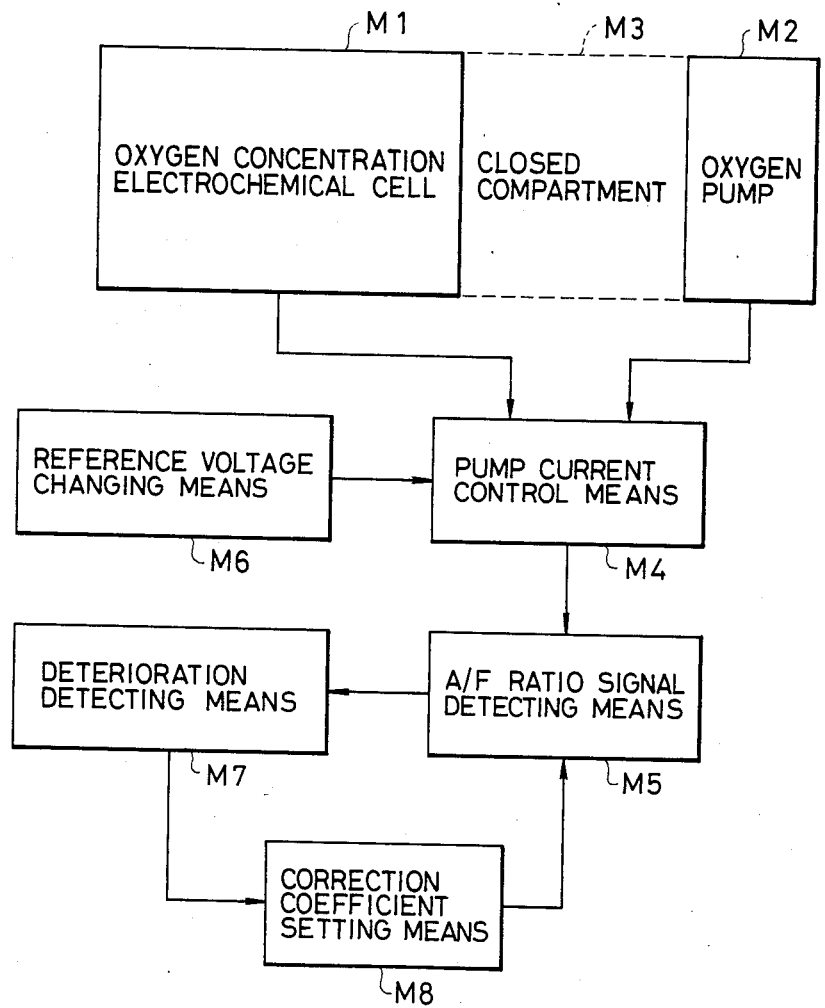
FIG. 2 is a block diagram of the A/F ratio sensor in accordance with a second embodiment of the present invention.
Figure 3:
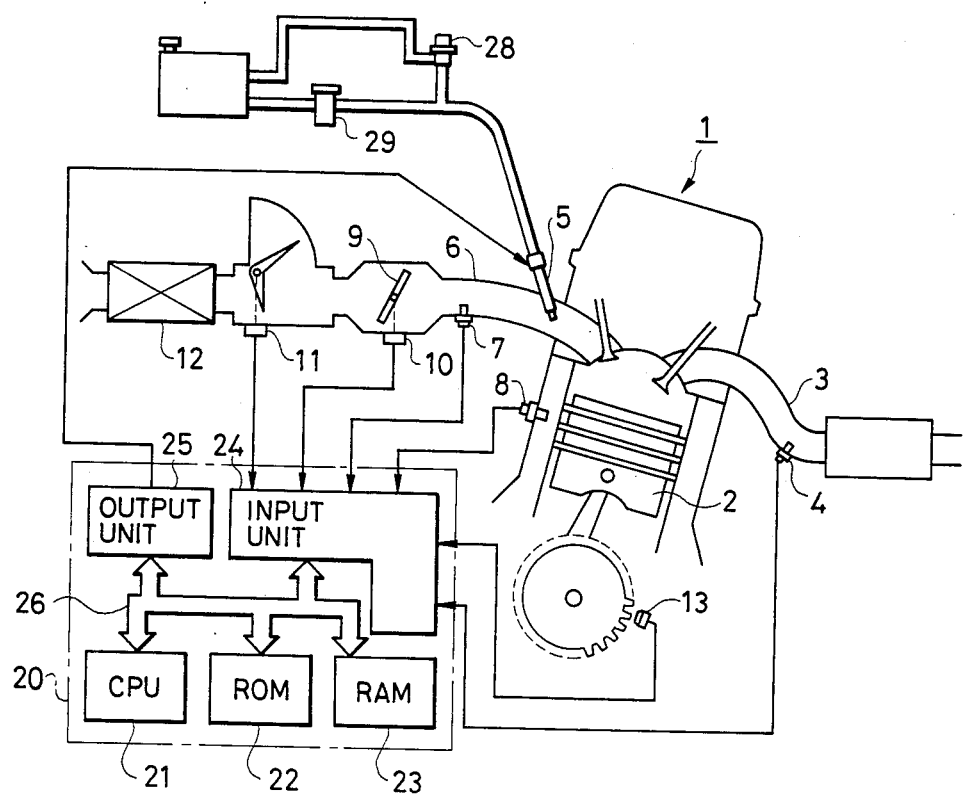

FIG. 3 is a schematic diagram of an internal combustion engine with which an A/F ratio sensor of the present invention in accordance with the embodiment is employed. In FIG. 3, reference numeral 1 represents the engine, 2 is a piston, 3 is an exhaust manifold 3 for detecting the A/F ratio of an air/fuel mixture supplied to the engine 1, 5 is a fuel injection nozzle provided for each of the cylinders to supply the fuel, 6 is a suction manifold, 7 is a sensor mounted through the wall of the manifold 6 for detecting the temperature of the air taken into the manifold, 8 is a sensor for detecting the temperature of the coolant used to cool the engine 1, 9 is a throttle valve, 10 is a sensor for detecting the degree of opening in the valve 9, 11 is an air flow meter, 12 is a cleaner for cleaning the air taken into the manifold 6, and 13 is a sensor that produces a signal proportional to the rotational speed of the engine 1.

The system shown in FIG. 3 also includes a microcomputer-operated electronic control circuit 20 composed of a central processing unit (CPU) 21 that receives output data from each of the sensors mentioned above, performs mathematical manipulation on that data in accordance with a predetermined control program, and which controls the fuel injection by driving the injection valve 5 in a manner adapted to the state of engine operation; a read-only memory (ROM) 22 preloaded with the control program to be executed by CPU 21 and other data such as maps; a random access memory (RAM) 23 that provides for temporary read/write of sensor outputs into the electronic control circuit 20 and any other data that is necessary for mathematical operations; an input unit 24 that includes a waveform-shaping circuit and an A/D converter associated with the signal from each sensor, as well as a multiplexer that provides selective delivery of the shaped digital signal into CPU 21, an output unit 25 that supplies a drive signal to the fuel injection valve 5 in accordance with the fuel injection that is determined by mathematical computations performed in CPU 21; and a bus line 26 that provides data-transmitting interconnections between the CPU 21, ROM 22, RAM 23, input unit 24 and output unit 25. The drive signal produced by the electronic control circuit 20 is sent to the fuel injection valve 5, through which fuel coming from a fuel pump 29 at a pressure controlled by a regulating valve 28 is supplied into the engine 1.

The oxygen sensor 4 is the major component of the system shown in FIG. 3 and incorporates the concepts of the present invention. The sensor 4 in this particular embodiment includes the oxygen concentration electrochemical cell M1, the oxygen pump M2 and the closed compartment M3 which accepts a limited inflow of the exhaust gas.

Figure 4:
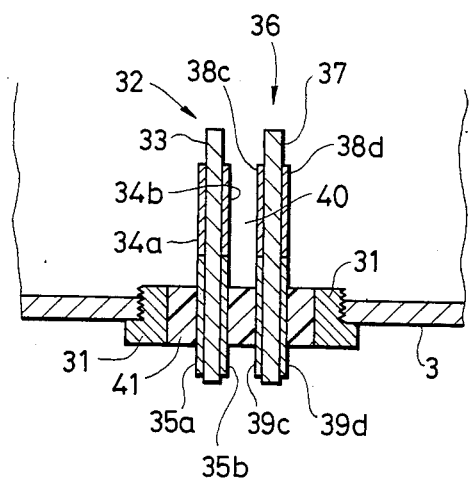
Figure 5:
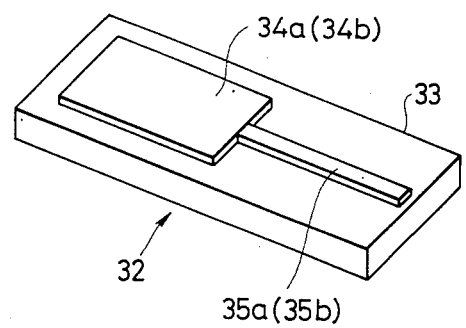

FIG. 4 shows a cross section of the oxygen sensor 4 as it is attached to the exhaust manifold 3 by mounting through an attachment hole together with a fastening member 31. Indicated at 32 is an oxygen concentration electrochemical cell which, as shown in FIG. 5, is composed of a tubular ion-conductive solid electrolyte 33 provided on opposite sides with a set of porous platinum electrode layers 34a and an output pickup platinum electrode 35a and another set of porous platinum electrode layers 34b and an output pickup platinum electrode 35b. The tubular solid electrolyte 33 may be formed of fully or partially stabilized zirconia, thoria or ceria and have a thickness of about 0.5 mm. Each of the platinum electrodes is formed by a thick-film deposition technique and has an approximate thickness of 20 microns. Indicated at 36 is an oxygen pump constructed in the same manner as the oxygen concentration electrochemical cell 32, having a set of porous platinum electrode layers 38c and a platinum electrode 39c and another set of porous platinum electrode layers 38d and a platinum electrode 39d formed on opposite sides thereof.

The oxygen concentration electrochemical cell 32 and the oxygen pump 36 are disposed in a face-to-face relationship with a heat-resistant and insulating spacer 41 inserted so as to form a gap 40 having a width of about 0.1 mm. The assembled cell 32 and pump 36 are fastened to the exhaust manifold 3 by means of a member 31. In the embodiment shown, this gap 40 formed by the cell 32 and the pump 36 provides the closed compartment M3 which accepts a limited inflow of the exhaust.

As already discussed, the pump current control circuit M4 controls the pump current flowing through the oxygen pump 36 so as to maintain the output voltage of the oxygen concentration electrochemical cell 32 at a constant level, and the A/F ratio signal detection circuit M5 detects the resulting pump current and extracts a signal indicative of the A/F ratio of the air/fuel mixture being supplied into the engine. The two circuits M4 and M5 combine to serve as an A/F ratio signal detection circuit, which is hereunder described in more detail.

Figure 6:
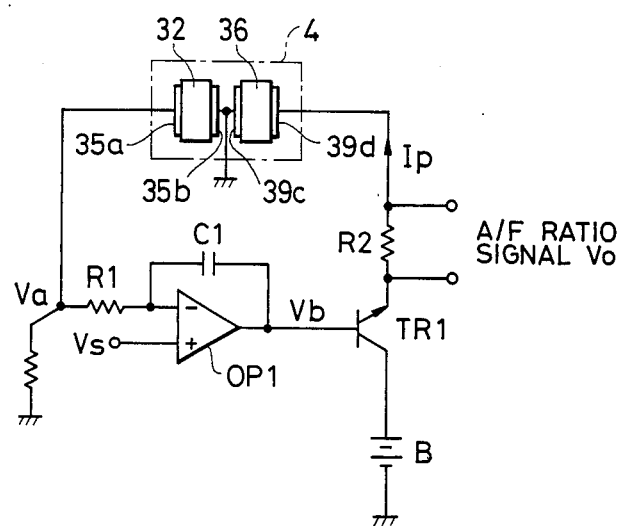

As shown in FIG. 6, the two principal components of this A/F ratio signal detection circuit are an operational amplifier OP1 and a transistor TR1. The platinum electrode 35b on the oxygen concentration electrochemical cell 32 and the platinum electrode 39c on that side of the oxygen pump 36 which faces the cell 32 are connected to ground. The other platinum electrode 32a on the cell 32 is connected to the inverting input of OP1 by way of a resistor R1, while the platinum electrode 39d on the other side of the pump 36 is connected to the emitter of TR1 by way of a resistor R2.

The operational amplifier OP1 has a capacitor C1 coupled between its inverting input terminal and its output terminal so as to provide an integrating circuit to thus produce a control signal $V_b$ that is proportional to the integral of the difference between a reference voltage $V_s$ fed to the non-inverting input terminal of OP1 and a voltage $V_a$ detected by the oxygen concentration electrochemical cell 32.

The base of the transistor TR1 is connected to the output terminal of OP1 so that the current applied from a battery B to the collector will be controlled as a pumping current Ip through the oxygen pump 36 in response to the control signal $V_b$. The resistor R2 inserted between the emitter of TR1 and the oxygen pump 36 functions to detect the pumping current Ip as a voltage signal, and the voltage across R2 provides an A/F ratio signal $V_o$.

By configuring the A/F ratio signal detection circuit as shown above, the oxygen pump 36 will operate to pump oxygen from the gap 40 into the exhaust gas so that the voltage $V_a$ generated by the oxygen concentration electrochemical cell 32 in accordance with the differential oxygen partial pressure between the gap 40 and the exhaust will be maintained at the predetermined reference voltage $V_s$. The resulting pump current Ip may be detected to provide the oxygen concentration of the exhaust or the A/F ratio of the mixed gas on which the engine 1 is operating.

The A/F ratio signal detection circuit described above is provided to the input unit of the electronic control circuit 20, which performs A/F ratio control of the engine 1 on the basis of the detected A/F ratio signal $V_o$. When the engine 1 starts to run without fuel supply, the electronic control circuit 20 not only performs engine control, but also performs diagnostic checking of the oxygen sensor 4, and if any abnormal A/F ratio signal is found to be outputted from the A/F ratio detector circuit, the coefficient for correcting that signal is computed. The sequence of this diagnostic checking of the oxygen sensor is hereunder described with reference to the flowchart shown in FIG. 7.

Figure 7:
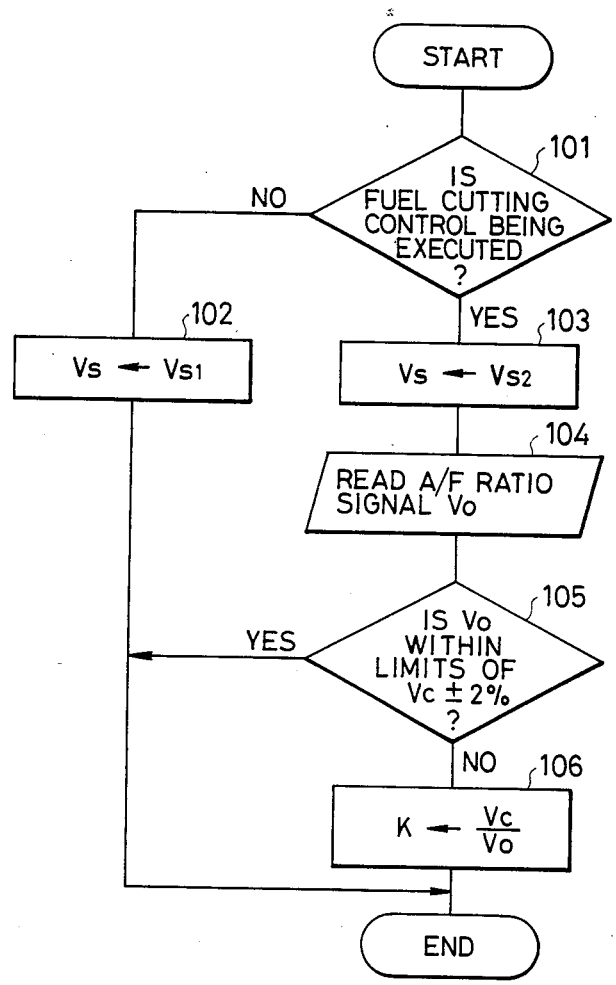

As illustrated in FIG. 7, the diagnostic checking of the sensor incorporated in the embodiment shown starts with step 101 to determine whether the engine 1 is under A/F ratio control for operation without fuel supply. If the engine 1 is found to be running with fuel supply, the sequence proceeds to step 102, wherein the reference voltage $V_s$ applied to OP1 in the A/F ratio detector circuit is set to $V_{s1}$ and the diagnostic routine ends. If the engine 1 is running without fuel supply, the sequence proceeds to step 103, wherein $V_s$ is set to $V_{s2}$ in preparation for execution of subsequent step 104.

Figure 8:
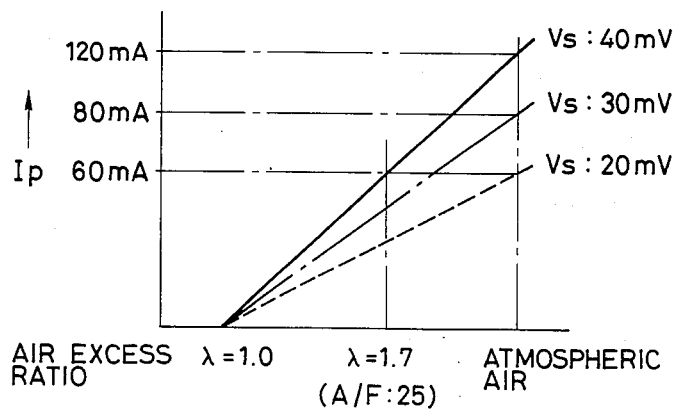

The value of $V_{s1}$ to which the reference voltage $V_s$ is set in step 102 may be selected at about 40 mV so that the pump current Ip flowing through the oxygen pump 36 at the most lean A/F ratio (typically about 25) during engine operation will be controlled at a relatively large value (60 mA) that does not exceed a maximum permissible level (80 mA) determined with a view to avoiding deterioration of the oxygen pump 36 (see FIG. 8). In step 103, the reference voltage $V_s$ is set to $V_{s2}$ which value is selected at about 20 to 30 mV, which is much lower than the value of $V_{s1}$ (40 mV), so that the pump current Ip flowing when the engine is running without fuel supply will not exceed the maximum permissible level (80 mA). The reasons for selecting such a small value are as follows: the concentration of atmospheric oxygen is detected when the engine is running without fuel supply, and if the oxygen pump is controlled with the reference voltage $V_{s1}$ being fixed to 40 mV, the amount of the pump current flowing through the oxygen pump will be increased to an excessively high level (120 mA).

In subsequent step 104, the A/F ratio signal $V_o$ detected as a result of control with reference to the voltage $V_{s2}$ is read and the sequence proceeds to 105, wherein determination is made as to whether the A/F ratio signal $V_o$ is within the limits of $\pm 2\%$ of the predetermined value $V_c$. If $V_o$ is within the limits of $V_c \pm 2\%$, the oxygen sensor 4 is found to have no problem and the diagnostic routine ends.

If, on the other hand, the A/F ratio signal $V_o$ is found to be outside the limits of $V_c \pm 2\%$, the sequence proceeds to the subsequent step 106, wherein $V_c/V_o$ is computed as a correction coefficient K used for attaining the proper A/F ratio signal $V_o$ when the engine is running with fuel supply, and then the diagnostic routine ends. The thus-computed correction coefficient K is used to correct the A/F ratio signal $V_o$ that is read when the engine resumes operation with fuel supply.

To summarize the operation of the embodiment shown above, the reference voltage $V_s$ for A/F ratio control to be performed when the engine is running without fuel supply is adjusted to the value $V_{s2}$, which is smaller than the value $V_{s1}$ used for performing the control when the engine is running with fuel supply, so that the pumping current Ip flowing through the oxygen pump 36 will not be increased to an excessively large amount to cause deterioration of the pump. The oxygen sensor 4 is found to have deteriorated if the A/F ratio signal $V_o$ detected for the reference voltage $V_{s2}$ is outside the limits of $V_c \pm 2\%$. If deterioration of the sensor is detected, the correction coefficient K for the A/F ratio signal $V_o$ is computed on the basis of the detected value of the A/F ratio signal $V_o$ and the reference value $V_c$, and the A/F ratio signal $V_o$ detected from the deteriorated sensor performing A/F ratio control is corrected to a value that is indicative of the actual A/F ratio.

Therefore, by using the A/F ratio sensor in accordance with the embodiment shown above, deterioration of the oxygen sensor 4 that may occur when the engine 1 is running without fuel supply can be prevented and, even if such deterioration occurs, the detected A/F ratio signal $V_o$ will be corrected to the normal value. Because of these features, a single oxygen sensor may be employed for the purpose of performing reliable A/F ratio control over an extended period.

In the embodiment described above, the correction coefficient K for the A/F ratio signal $V_o$ is computed in step 106 (FIG. 7) after deterioration of the oxygen sensor 4 is detected in step 105. In another embodiment, if the oxygen sensor 4 is found to have deteriorated, feedback control of the A/F ratio for the engine running with fuel supply may be inhibited and this fact displayed on the dashboard to inform the driver of the need for replacing the sensor 4. If the deterioration of the oxygen sensor is serious, it may be impossible to correct the detected A/F ratio to the normal value even if it is modified by computation of the coefficient K. Therefore, in still another embodiment of the present invention, if the correction coefficient K computed in step 106 is not within the limits of $1 \pm 20\%$, feedback control of the A/F ratio signal for the engine running with fuel supply is inhibited and this fact is displayed on the dashboard so as to urge the driver to replace the deteriorated oxygen sensor.

In the oxygen sensor in accordance with the embodiment shown in detail above, the two sensing elements, each consisting of a solid electrolyte with a porous platinum electrode layer formed on both sides, are disposed in a face-to-face relationship with a small gap therebetween so as to provide a closed compartment that accepts a limited inflow of the exhaust gas. If desired, part of the wall defining the closed compartment may be formed of a heat-resistant material such as a ceramic or metal, with an aperture formed to admit the inflow of the exhaust gas, and the remaining part of the wall is formed of the two sensing elements.

In the oxygen sensor of the embodiment shown in described above, the porous electrode layer on that side of the oxygen concentration electrochemical cell which is opposite the side facing the closed compartment is in contact with the exhaust gas, and the A/F ratio signal that is obtained is limited to values in the lean region. In order to eliminate this inconvenience, the sensor may be constructed so that the porous platinum electrode formed on that side of the oxygen concentration electrochemical cell which is opposite the side facing the close compartment is in contact with the atmospheric air. In this modified design, the pumping current may be controlled in the two directions to attain a predetermined value of the concentration of oxygen in the closed compartment so that an A/F ratio signal that changes linearly over the full operating range including the rich, stoichiometric and lean regions can be detected. This oxygen sensor design may be effectively employed for the purpose of A/F ratio control of an internal combustion engine and any deterioration of the sensor can be correctly detected by following the control sequence described in the foregoing.

As described in detail hereinabove, the A/F ratio sensor for use with an internal combustion engine in accordance with the first embodiment of the present invention includes a reference value changing circuit that alters the reference voltage for the pumping current control circuit to a small value when the engine is operating without fuel supply, and a deterioration detecting circuit that detects deterioration of the sensing elements by comparing the reference value with the A/F ratio signal detected by the A/F ratio signal detection circuit when the engine is running without fuel supply. This arrangement is effective in preventing not only the passage of an extremely large current through the oxygen pump while the engine is running without fuel supply, but also erroneous feedback control of the A/F ratio that may result from the use of deteriorated sensing elements.

The A/F ratio sensor for use with an internal combustion engine in accordance with the second embodiment of the present invention includes, in addition to the aforementioned reference value changing circuit and deterioration detection circuit, a correction coefficient setting circuit that sets a coefficient for correcting the A/F ratio signal being detected while operating with deteriorated sensing elements. Even if the exhaust inlet aperture in the closed compartment is clogged or either the oxygen pump or the oxygen concentration electrochemical cell itself is deteriorated, the sensor apparatus of the second aspect of the invention will enable the detected A/F ratio signal to be corrected to the accurate value, thereby ensuring continued feedback control of the A/F ratio in a precise manner.

I claim:
1. An air/fuel ratio sensor apparatus for use with an internal combustion engine, comprising:
two sensing elements, each comprising an oxygen-ion-conductive solid electrolyte having a porous electrode formed on both sides thereof;
a closed compartment that limits inflow of exhaust, said two sensing elements defining at least portions of said compartment;
pump current control means, using one of said sensing elements as an oxygen concentration electrochemical cell and the other sensing element as an oxygen pump, for controlling pump current flowing through said oxygen pump such that an electromotive force generated by said oxygen concentration electrochemical cell is maintained at a preset reference voltage;
air/fuel ratio signal detecting means for detecting the controlled pump current and producing an associated air/fuel ratio signal,
said sensor further including:
reference voltage changing means for, when the internal combustion engine is running without fuel supply, changing said reference voltage for said pump current control means to a value smaller than that when the engine is running with fuel supply;

deterioration detecting means for, when the engine is running without fuel supply, detecting deterioration of said two sensing elements by comparing the air/fuel ratio signal produced by said air/fuel ratio signal detecting means with a preset reference value; and correction coefficient setting means for, when deterioration of the sensing elements is detected by said deterioration detecting means, setting a coefficient for correcting an air/fuel ratio signal detected when the engine is running with fuel supply on the basis of both the air/fuel ratio signal detected during engine operation without fuel supply and said reference value.

* * * * *